United States Patent [19]

Chapman

[11] Patent Number: 4,871,309

[45] Date of Patent: Oct. 3, 1989

[54] APPARATUS FOR PREPARING SAMPLES

[75] Inventor: David J. Chapman, East Hawthorn, Australia

[73] Assignee: D. J. C. Electrical Engineering Pty. Ltd., Victoria, Australia

[21] Appl. No.: 222,722

[22] Filed: Jul. 21, 1988

[30] Foreign Application Priority Data

Aug. 6, 1987 [AU] Australia .................. PI3575

[51] Int. Cl.[4] .............................. F27B 14/00
[52] U.S. Cl. .................... 432/156; 432/157; 432/211
[58] Field of Search ............... 432/156, 157, 210, 211

[56] References Cited

U.S. PATENT DOCUMENTS

| 1,707,313 | 4/1929 | Merten | 432/197 |
| 3,790,338 | 2/1974 | Duca | 432/157 |
| 3,984,613 | 10/1976 | Reese | 432/156 |
| 4,033,564 | 7/1977 | Junghanns et al. | 432/211 |

Primary Examiner—Henry C. Yuen
Attorney, Agent, or Firm—Price, Heneveld, Cooper, DeWitt & Litton

[57] ABSTRACT

An apparatus for producing a sample is disclosed which has a tilting mechanism (12, 14, 22). The tilting mechanism has a crucible holder (70) releasably coupled thereto and a crucible (100), which is provided with a flange (102), is insertable into the crucible (70) so that the crucible can be tilted by the tilting mechanism. A dish (46) is supported by a support (44) so that the tilting mechanism can tilt the crucible (100) to pour the contents of the crucible into the dish (46). Burners (48 and 50) are provided for heating the contents of the crucible (100) and dish (46).

15 Claims, 5 Drawing Sheets

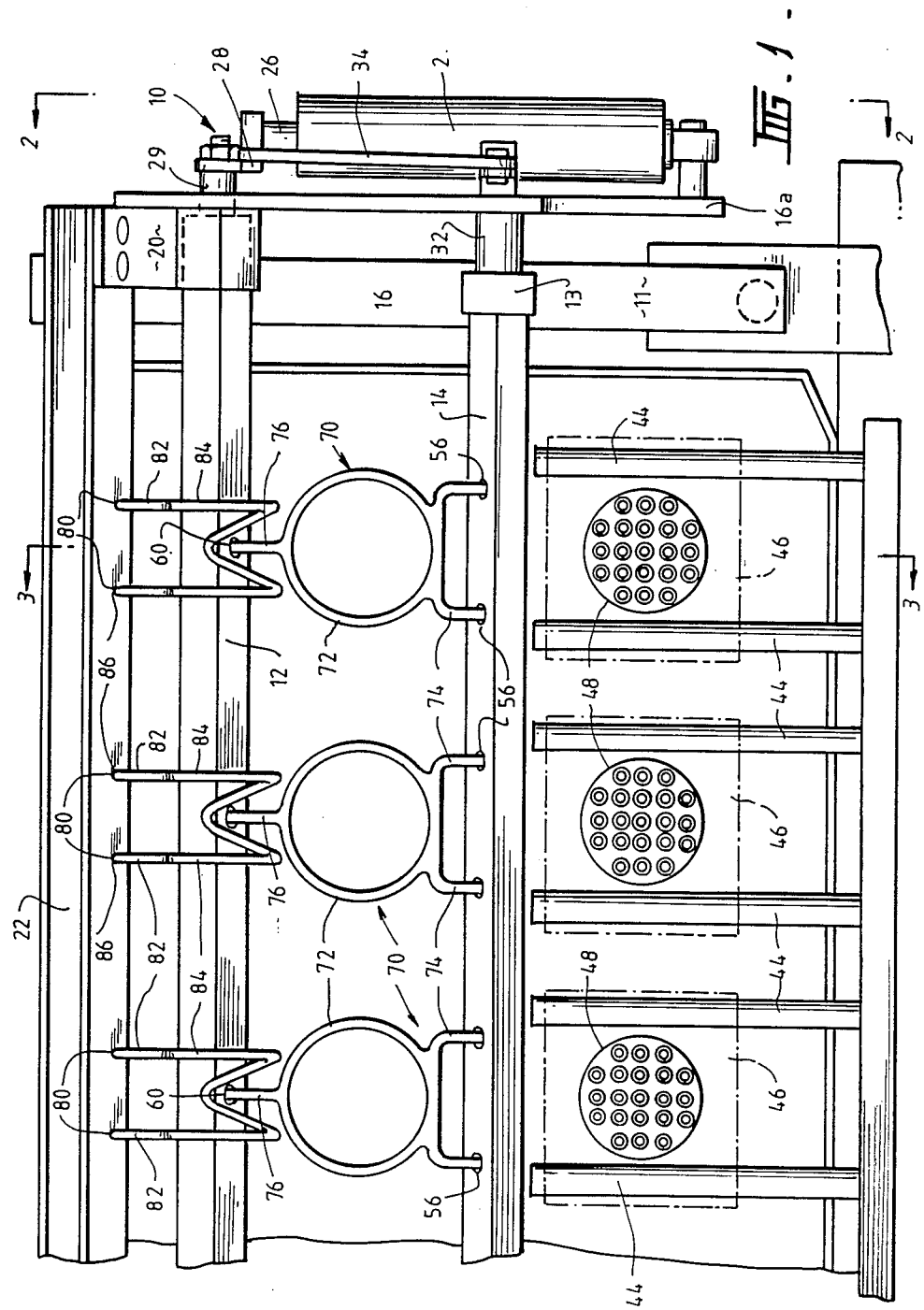

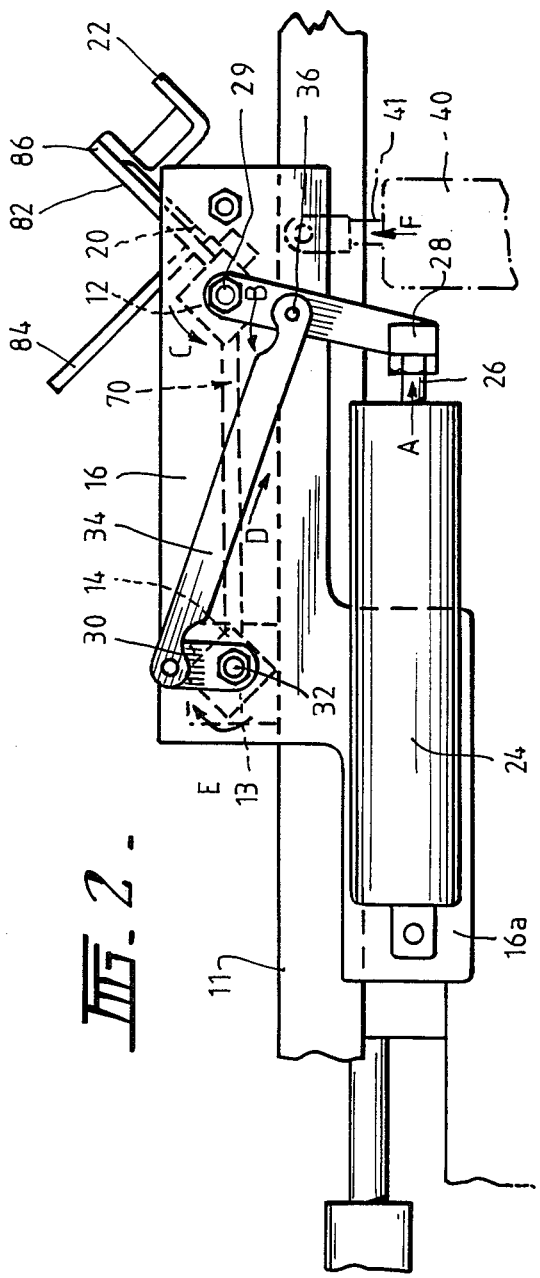

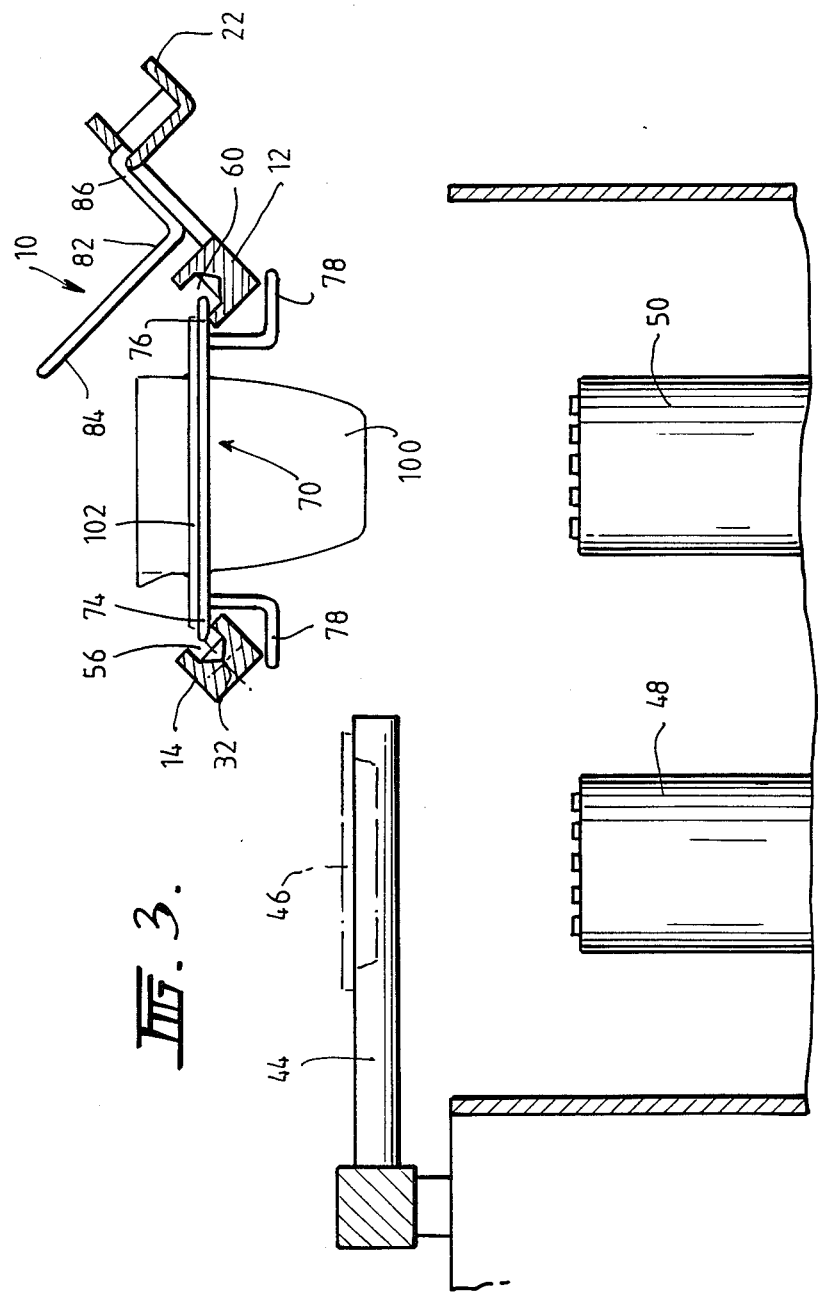

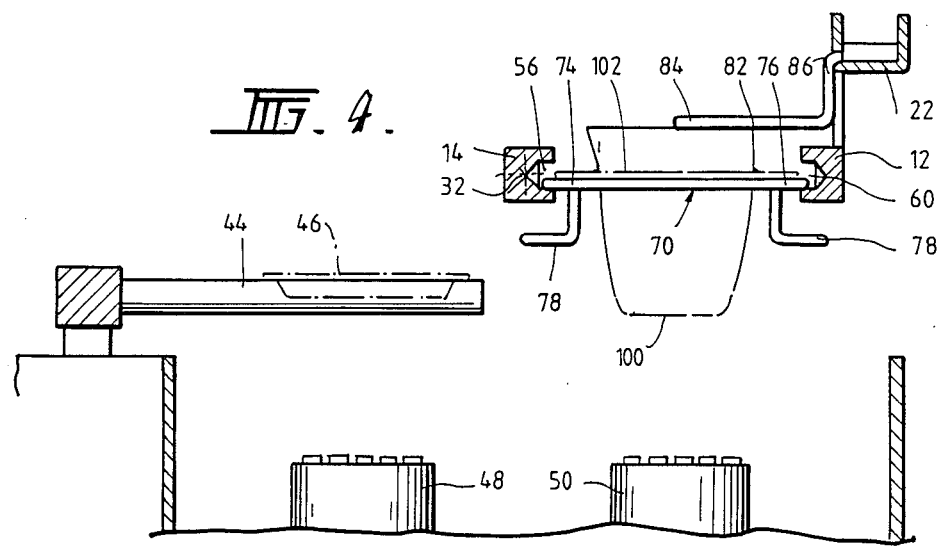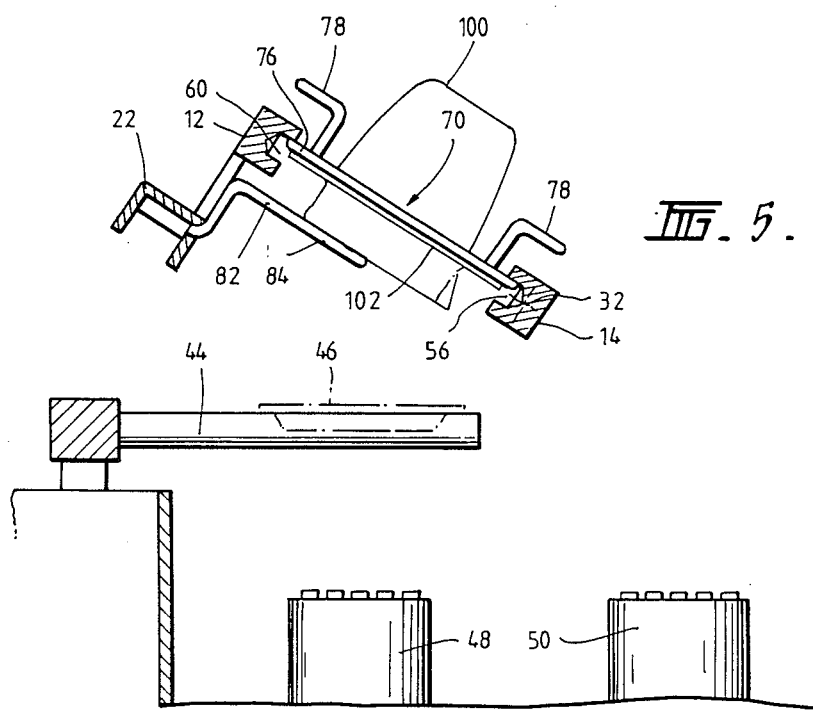

APPARATUS FOR PREPARING SAMPLES

This invention relates to an apparatus for preparing samples, and in particular, but not exclusively, an apparatus for preparing samples for use in mining industries, ceramics and brick production industries and the like.

In the above industries, it is often necessary to produce samples for analysis or for other purposes. A conventional apparatus for preparing such samples comprises a housing in which a number of burners are located. The apparatus includes a number of movable rails which grip a crucible and which can hold the crucible above a burner. The rails are movable so that the crucible can be tilted to tilt the contents of the crucible into a dish. The dish itself may be located in the apparatus above a burner. In order to prepare the sample, the material to be analyzed is poured into the crucible and is mixed with another substance such as lithium metaborate or lithium tetaborate. The sample and, lithium metaborate or lithium tetaborate is then mixed in the crucible above the burner and is poured into the dish so that the sample and the lithium metaborate or lithium tetaborate can be fused into a bead.

In view of the nature of the samples and substances used in such machines, the crucible and dishes in which the substances are mixed are made from platinum, gold or possibly rhodium or grain stabilized platinum. Thus, the crucibles and dishes are extremely expensive.

The conventional manner of supporting the crucible in the apparatus is to provide a number of pins on the crucible. The pins are attached to the crucible by soldering and are received in apertures in the tilting mechanism of the apparatus. A major drawback with the conventional apparatus is that if the crucible is not accurately located in the tilting mechanism, when the tilting mechanism is moved, the pins can be buckled or pushed through the crucible or pulled out of the crucible. If the pins are buckled or the crucible is damaged, the crucible is no longer of any use and must be melted down and remoulded. Thus, with the conventional system it is necessary for a number of crucibles to be available in the event that one is damaged and for damaged crucibles to be continually melted down and remoulded. The need to provide a number of crucibles for replacement purposes and then to melt down and remould the crucible is both expensive and time consuming.

The object of this invention is to provide an apparatus in which a crucible can be used to form a bead for analysis with little likelihood of damage to the crucible.

The invention may be said to reside in an apparatus for producing a sample, said apparatus comprising a tilting mechanism for tilting a crucible and a support mechanism for supporting a dish into which the contents of the crucible can be poured, said tilting mechanism including means for supporting a crucible holder, a crucible holder for location in said means such that the crucible can be located in the holder and the tilting mechanism tilted to pour the contents of the crucible into the dish.

Since the tilting mechanism supports a crucible holder and the crucible is merely located in the crucible holder, the crucible is not subject to damage since it itself is not gripped or retained by the tilting mechanism.

In the preferred embodiment of the invention the tilting mechanism includes a retainer for holding the crucible in the crucible holder when the tilting mechanism tilts the crucible.

Preferably the crucible holder comprises a generally circular frame having an opening into which the crucible is inserted and the crucible has a flange which abuts the frame so that the crucible is supported by the frame, said frame having a plurality of prongs which are received in apertures in the tilting mechanism to hold the crucible holder in the tilting mechanism. Preferably the crucible holder is permanently but releasably held in the tilting mechanism.

In a second aspect the invention may be said to reside in a crucible holder for location in a tilting mechanism of an apparatus for producing samples, said crucible holder having a frame member into which a crucible can be inserted to support the crucible, and a plurality of prongs which can be coupled to a tilting mechanism to attach the crucible holder to the tilting mechanism.

Preferably the prongs include generally L-shaped members for assisting engagement of the crucible holder to the tilting mechanism.

In a second aspect the invention provides a crucible for use in a sample preparation apparatus, said crucible having a flange on its outer periphery so that the crucible can be supported by the flange in a crucible holder which in turn is coupleable to a tilting mechanism of the sample preparation apparatus.

The invention also provides a burner for heating a sample, said burner having a main burner and a booster burner, wherein said main burner has a mixing chamber and said booster burner has a mixing chamber, said mixing chambers having means for introducing air and gas to the mixing chambers.

The invention still further provides a burner for heating a sample, said burner having a mixing chamber and an oxygen chamber, means for introducing an air and gas into said mixing chamber and means for introducing oxygen into said oxygen chamber means for delivering an air gas mixture from the mixing chamber to a burner upper surface, means for introducing oxygen from the oxygen chamber to the burner upper surface so that the air gas mixture and oxygen can be mixed and burnt above the upper surface.

A preferred embodiment of the invention will be described, by way of example, with reference to the accompanying drawings in which:

FIG. 1 is a plan view of part of an apparatus embodying the invention;

FIG. 2 is a view along the line 2—2 of FIG. 1;

FIG. 3 is a view along the line 3—3 of FIG. 1;

FIG. 4 is a view similar to FIG. 3 with a crucible supported in the apparatus;

FIG. 5 is a view similar to FIG. 3 with the crucible being tilted to enable the crucible to be poured.

Figure 6:
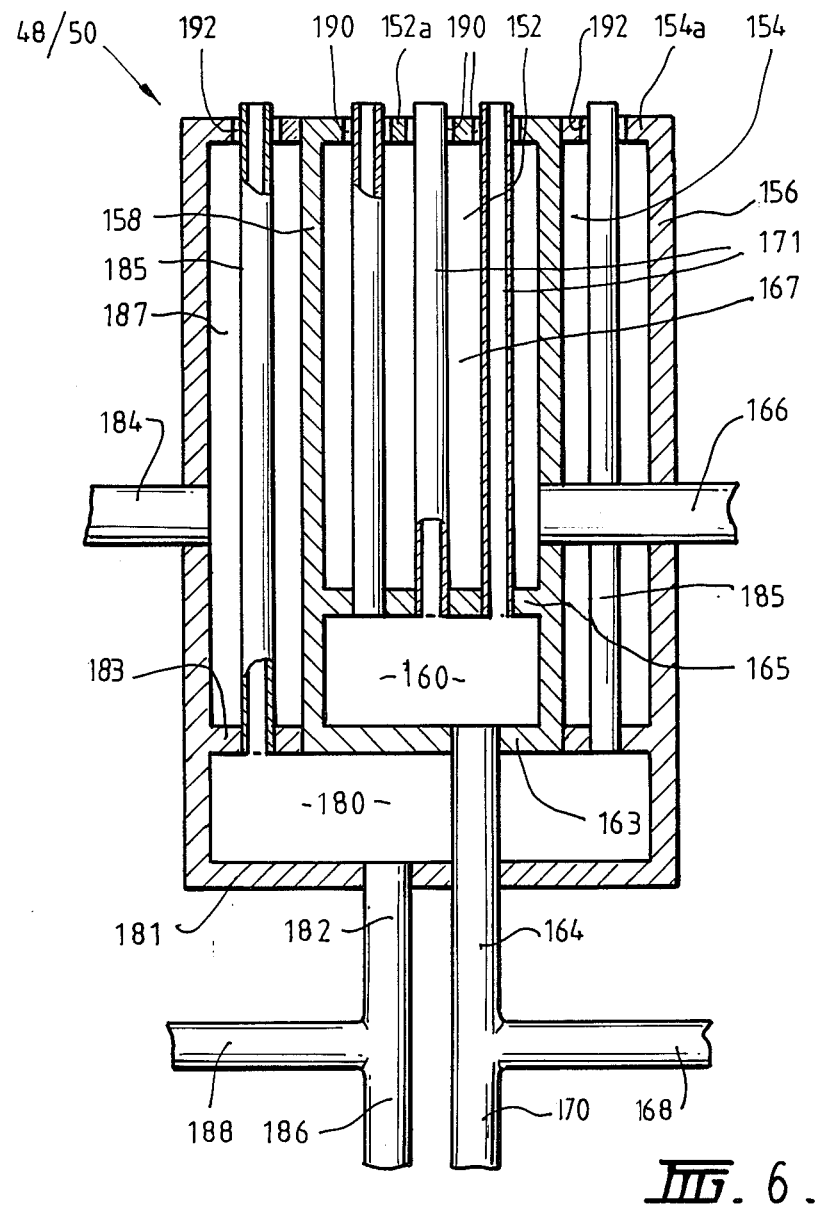
FIG. 6 is a view of a burner used in the preferred embodiment.

FIG. 1 and 2 shows part of an apparatus for producing samples. Such apparatus are generally known and only the part of the apparatus concerned with the preferred embodiment of the invention is shown. The apparatus generally comprises a tilting mechanism 10 which comprises a pair of rails 12 and 14 which are coupled together by plates 16 at each end of the apparatus. In FIG. 1 only one of the plates 16 is shown. The rail 12 has an upright member 20 which couples the rail 12 to a second rail 22.

The tilting mechanism 10 is attached to a portion 11 of the housing by blocks 13 (only one shown) in which a pivot pin 32, located at the ends of the rail 14, is journalled.

The plate 16 has a lower portion 16a to which is coupled a pneumatic or hydraulic cylinder 24. The cylinder 24 has a rod 26 which is coupled to a link 28. The link 28 is pivotally coupled at 29 to the rail 12. The pivot pin 32 has a link 30 extending upwardly which is pivotally coupled to a further link 34 which extends from one end of the link 30 to a mid point of the link 28 where it is also pivotally coupled about a pivot pin 36.

As shown in FIG. 2, in dotted lines, the apparatus includes a second hydraulic or pneumatic cylinder 40 which is arranged at the opposite end of the apparatus to that shown in FIGS. 1 and 2 and which is coupled to the plate 16 at the opposite end of the apparatus.

The apparatus also includes support members 44 for supporting dishes 46. As is best seen in FIG. 3, the dishes 46 are arranged above burners 48 (only one shown) and the crucible tilting mechanism 10 is arranged above a line of burners 50 (only one shown).

The rails 14 are provided with pairs of apertures 56 which are spaced apart by a prescribed distance. The pairs of apertures 56 are arranged in alignment with respective burners 50 in the row of burners 50. The rail 12 includes a number of apertures 60 which are arranged to be opposed to mid points between each set of apertures 56. The apertures 56 and 60 receive crucible holders 70 which comprise a generally circular frame member 72 which has two prongs 74 arranged at one end and a single prong 76 arranged at the other end. The prongs 74 are adapted to be received in the apertures 56 and the prongs 76 is adapted to be received in the aperture 60. As shown in FIG. 3, the prongs 74 and 76 can have L-shaped brackets 78 which engage about the rails 14 and 12 for assisting in holding the crucible holder 70 to the rails 14 and 12.

The rail 22 is provided with pairs of apertures 80 which receive retainers 82. The retainers 82 as best shown in FIGS. 2 and 3, are generally of L-shaped configuration (in side view) and have a retaining portion 84 and a rail engagement portion 86 which are substantially at right angles to one another. The retaining portion 84 is generally of W-shape in plane view. The rail engagement portion 86 has ends which are bent at right angles and which are received in the apertures 80. The crucible holders 70 are located between the rails 12 and 14 by causing the cylinder 24 to retract its rod 26. This then places the rails 12 and 14 into the position shown in FIGS. 2 and 3 where the apertures 56 and 60 are arranged approximately at 45° angles with respect to the vertical. In this position the crucible holder 70 can be easily inserted between the rails by locating the prongs 74 and 76 on edges of the apertures and the L-shaped brackets 78 so that they can extend beneath the rails 12 and 14. A crucible 100 is then inserted into the frame 72 so that a flange 102 on the outer surface of the crucible is supported on the frame 72. The pneumatic cylinder 24 is then operated so that the rod 26 is extended in the direction of arrow A shown in FIG. 2. This causes the link 28 to move in the direction of arrow B and to rotate the rail 12 in the direction of arrow C so that it is moved into the position shown in FIG. 4. Movement of the rail 12 also moves the rail 22 to which it is coupled via the upright 20 into the position shown in FIG. 4. Movement of the link 28 causes the link 34 to move in the direction of arrow D to rotate the link 38 and the rail 14 in the direction of arrow E. This brings the rail 14 into the position shown in FIG. 4 where the crucible holder 70 is securely held within the apertures 56 and 60 in the rails 12 and 14. In this position the retainer 82 is also in abutment with the crucible 100 and holds the crucible 100 securely in the crucible holder 70. The appropriate materials may then be placed in the crucible and melted by heat from the burner 50.

In order to tip the contents of the crucible 100 into the dish 46, the pneumatic cylinder 40 at the opposite end of the apparatus is operated to push its rod 41 in the direction of arrow F. The rod 41 is coupled to the bracket 16 at the opposite end of the apparatus and hence the rails 12 and 14 which are coupled between the respective brackets and hence movement of the rod 41 in the direction of arrow F tilts the entire tilting mechanism comprised of the brackets 16, the rails 12 and 14, the links 28, 34 etc. and the cylinder 24 about the axis of the rod 14 (namely pivot pin 32) so that the tilting mechanism is moved into the position shown in FIG. 5. In this position the contents of the crucible 100 is poured into the dish 46 while the crucible is securely held within the crucible holder by the retainer 82.

In order to return the crucible to its usual position, the rod 41 is retracted to draw the tilting mechanism back into the position shown in FIG. 4. The cylinder 24 may then be activated to draw the rod 26 in a direction opposite to the arrow A so that the rods 12 and 14 are pivoted into the position shown in FIG. 3 to enable the crucible to be removed. The crucible holder 70 can be permanently retained between the rails 12 and 14 although it should be understood that the crucible holder can be easily removed when the rails 12 and 14 are in the position shown in FIG. 3.

Since the crucible itself is supported in a crucible holder which is retained between the rails 12 and 14 the crucible is not damaged when the rails 12 and 14 are pivoted into the position shown in FIG. 4 and thus the apparatus of this invention is much less likely to cause damage to the crucible as compared with prior art devices.

As is shown in FIG. 6 the burner 48 and/or the burner 50 may comprise a main burner 152 and a booster burner 154. The booster burner 154 and main burner 152 are generally concentrically arranged with the main burner 152 being in the center of the booster burner 154. The booster burner 154 comprises an annular upper surface 154a and a depending cylindrical side wall 156. The main burner 152 comprises an upper generally circular surface 152a and a depending cylindrical side wall 158. A mixing chamber 160 is provided in the bottom portion of the main burner 152. The mixing chamber is defined between a base 163 and an intermediate panel 165. The base 163 receives an inlet tube 164 which is provided with two branches 168 and 170 for introducing air and gas respectively into the inlet tube 182 and then into the mixing chamber 160. An oxygen inlet pipe 166 communicates with a space 167 defined between the intermediate panel 165 and the top surface 152a. The mixing chamber 160 is provided with a plurality of tubes 171 which extend upwardly from the intermediate panel 165 and through openings 190 in the upper surface 152a. The openings 190 are of slightly larger diameter than the tubes 171 so that oxygen introduced into the space 167 can leave the space through the openings 190. The tubes 171 convey an air gas mixture mixed in the mixing chamber 160 to the region above the upper surface 152a of the burner so that a flame can be sustained above the upper surface 152a.

The unique mixing of air gas in the chamber 160 and then further mixing with oxygen above the surface 152a enables the flame to be carefully controlled by suitable control of the amount of air, gas and oxygen supplied and also provides extremely good flame characteristics for melting samples of the type previously described.

The booster burner 154 is provided with a mixing chamber 180 which is defined between a base 181 and intermediate panel 183. An inlet pipe 182 communicates with the mixing chamber 180 through the base 181. The pipe 182 has a pair of branches 186 and 188 for applying air and gas respectively to the pipe 182. A plurality of tubes 185 communicate with the mixing chamber 180 and extend from the intermediate panel 183 through openings 192 in the surface 154a. Once again, the openings 192 are of slightly larger diameter than the tubes 185. An oxygen inlet pipe 184 is coupled to the side wall 156 for supplying oxygen to the space 187 between the intermediate panel 183 and the upper surface 154a.

Air and gas which is mixed in the chamber 180 is supplied to the region immediately above surface 154a by the tubes 185. Oxygen is also supplied to that region from the openings 192.

In order to heat a sample in the crucible 100 or dish 46, the air gas mixture is applied to the main burner 152 so that the air and gas is mixed in the mixing chamber 160 and then to the region immediately above the upper surface 152a via the tubes 171. Oxygen is applied to the space 167 via the pipe 166 and passes through the openings 190 into that region. Thus, a flame can be sustained above the upper surface 152a.

If desired the booster burner can be ignited by supplying air and gas to the mixing chamber 180 via the pipe 182 so that the air and gas is mixed in the chamber 180 and provided to the region above the upper surface 154a via the tubes 185. Oxygen is supplied to the space 187 via the pipe 184 so that it is also supplied to that region through the holes 192. The booster burner can be used for swirling crucible 100. When the booster burner is ignited the heat remains approximate the same per unit area but is applied over a greater area of the crucible 100 for swirling the crucible 100. Once again, the air gas mixture and the oxygen which is provided to the region above the upper surface 154a provides ideal characteristics for sustaining the flame for preparing samples of the type previously mentioned.

Since modification within the spirit and scope of the invention may readily be effected by persons skilled within the art, it is to be understood that this invention is not limited to the particular embodiment described by way of example hereinabove.

The claims defining the invention are as follows:

1. An apparatus for producing a sample, said apparatus comprising a tilting mechanism for tilting a crucible and a support means for supporting a dish into which the contents of the crucible can be poured, said tilting mechanism including means for supporting a crucible holder, a crucible holder for location in said means such that the crucible can be located int eh holder and the tilting mechanism actuated to pour the contents of the crucible into the disk, and wherein the tilting mechanism includes retainer means for holding the crucible in the crucible holder when the tilting mechanism tilts the crucible, pivot means supporting said retainer means for pivotal movement between crucible release and crucible clamping position.

2. The apparatus of claim 1, wherein the crucible holder comprises a generally circular frame having an opening into which the crucible is inserted and the crucible has a flange which abuts the frame so that the crucible is supported by the frame, said frame having a plurality of prongs which are received in apertures in the tilting mechanism to retain the crucible holder in the tilting mechanism.

3. The apparatus of claim 1, wherein the crucible holder is positively but releasably held in the tilting mechanism.

4. The apparatus of claim 1, wherein the crucible holder has a frame member into which the crucible can be inserted to support the crucible, and a plurality of prongs which can be coupled to a tilting mechanism to attach the crucible holder to the tilting mechanism.

5. The crucible holder according to claim 4, wherein the prongs include generally L-shaped members for assisting engagement of the crucible holder to the tilting mechanism.

6. An apparatus for producing a sample, said apparatus comprising a tilting mechanism for tilting a crucible and a support means for supporting a dish into which the contents of the crucible can be poured, said tilting mechanism including means for supporting a crucible holder, a crucible holder supported in said means such that the crucible can be located in the holder and the tilting mechanism actuated to pour the contents of the crucible into the dish, said means for supporting the crucible holder comprising a pair of rails, said crucible holder having engaging means for engaging the pair of rails to support the crucible between the pair of rails, releasable clamp means for holding the crucible in rail engaged position while the tilting mechanism is actuated.

7. The apparatus according to claim 6 wherein a plurality of crucible holders are provided between said pair of rails.

8. The apparatus of claim 6 wherein said rails include apertures and said crucible holder includes prongs which are received in said apertures to positively but releasably retain the crucible holder between the rails.

9. The apparatus according to claim 6, wherein pivot means are provided for pivotally mounting said rails about their longitudinal axes, said rails being coupled to actuating means for pivoting the rails about their respective axes to locate the rails in a first position in which the crucible holder can be placed between the rails, said actuating means also being adapted for pivoting said rails about the axes into a second position wherein the crucible holder is locked between the rails.

10. The apparatus according to claim 6 wherein the rails are mounted in a support frame and said tilting mechanism comprises ram means for pivoting said support frame and said rails.

11. An apparatus for supporting a crucible during production of a sample, said apparatus having a pair of spaced rail members, a crucible supporting frame supported on and between the rail members, said rail members being movable between frame releasing and frame clamping positions; said frame having a central opening for receiving a crucible; one of said rail members having an arm extending toward said crucible which arm is moved by said rail member into a crucible clamping position positively holding the crucible against any displacement from said frame when the rail member on which the arm is mounted is moved to frame clamping position, said arm being movable to crucible release position when said member is moved in the opposite direction; means for rotating the frame and crucible to substantially inverted discharge position while it remains clamped.

12. An apparatus as described in claim 11 wherein the crucible has a radially extending flange between its ends, said flange being clamped between said frame and said arm when in crucible clamping position.

13. An apparatus as described in claim 11 wherein said members having channels for receiving said frame, said channels having a cross-sectional shape such that said frame can be removed by lifting it from said channels when said members are rotated to release position and said channels enclose the peripheral portions of said frame when said members are counter-rotated to clamping position.

14. An apparatus as described in claim 11 wherein said arm engages that portion of the open end of said crucible which remains uppermost during inversion of said crucible.

15. An apparatus for producing a sample, said apparatus comprising a tilting mechanism for tilting a crucible and a support means for supporting a dish into which the contents of the crucible can be poured, said tilting mechanism including means for supporting a crucible holder, a crucible holder for location in said means such that the crucible can be located in the holder and the tilting mechanism actuated to pour the contents of the crucible into the dish, and wherein &.he tilting mechanism includes retainer means for holding the crucible in the crucible holder when the tilting mechanism tilts the crucible, holding means supporting said retainer means for movement between crucible release and crucible clamping position.

* * * * *